United States Patent [19]
Arrowsmith et al.

[11] Patent Number: 6,043,639
[45] Date of Patent: Mar. 28, 2000

[54] METHOD AND APPARATUS FOR REAL-TIME DETECTION OF AIRBORNE CONDUCTIVE CONTAMINANTS

[75] Inventors: Peter Arrowsmith, North York; John D. Duff, Mississauga, both of Canada

[73] Assignee: Celestica International Inc., Toronto, Canada

[21] Appl. No.: 08/980,773

[22] Filed: Dec. 1, 1997

[51] Int. Cl.[7] ............................. G01N 15/02; G01N 27/04
[52] U.S. Cl. ............................................. 324/71.4; 324/464
[58] Field of Search ................................... 324/455, 464, 324/71.4

[56] References Cited

U.S. PATENT DOCUMENTS

| | | | |
|---|---|---|---|
| 3,078,709 | 2/1963 | Clark | 324/71.4 |
| 4,070,660 | 1/1978 | Tauber | 340/236 |
| 4,158,610 | 6/1979 | Bauer | 324/455 |
| 4,769,609 | 9/1988 | Masuda | 324/71.4 |
| 4,839,602 | 6/1989 | Pletcher | 324/57 |
| 5,118,410 | 6/1992 | Rumberger | 210/85 |
| 5,150,036 | 9/1992 | Pourprix | 324/71.4 |
| 5,457,396 | 10/1995 | Mori et al. | 324/724 |
| 5,596,266 | 1/1997 | Mori et al. | 324/71.1 |

FOREIGN PATENT DOCUMENTS 157-003  10/1985  European Pat. Off. .............. 324/71.4

*Primary Examiner*—Josie Ballato
*Assistant Examiner*—Jose M. Solis
*Attorney, Agent, or Firm*—Alex Porat; Blake, Cassels & Graydon

[57] ABSTRACT

There is provided a detector for detecting conductive contaminants entrained in an airflow. The detector comprises first and second electrically conductive meshes mounted in a spaced apart relationship to provide an operational gap. Each of the meshes is sized to provide a relatively large surface for substantially intersecting the airflow and is sufficiently porous so as not to substantially attenuate the airflow. The meshes form part of an energizable electric circuit wherein the operational gap constitutes a discontinuity of the circuit. The detector includes a capacitor connected in parallel to the portion of the circuit containing the operational gap for releasing a charge stored in the capacitor through the circuit discontinuity when one of the conductive contaminants simultaneously contacts the first and second meshes. The detector further provides for indication of a discharge of the capacitor and thereby the presence of one of the airborne conductive contaminants entrained in the airflow.

19 Claims, 3 Drawing Sheets

METHOD AND APPARATUS FOR REAL-TIME DETECTION OF AIRBORNE CONDUCTIVE CONTAMINANTS

FIELD OF INVENTION

The invention relates to apparatus and methods for the real time detection of conductive airborne contaminants liable to cause short circuit failure of electrical and computer equipment.

BACKGROUND OF INVENTION

Airborne conductive contaminants can cause short-circuit failure of electrical and computer equipment. Equipment, such as power supplies, that utilize forced air cooling and have high densities of electrical circuits with high voltages across small node gaps are particularly susceptible. The types of electrically conductive contamination include metallic particulates, whiskers and shards, fragments of wires, and fibres used in anti-static floor coverings. These particulates become entrained in the airflow used to cool the electrical equipment. Metal whiskers are particularly hazardous to electrical equipment because the whiskers are extremely light, having a typical diameter of about 1 micron and a length of about 0.5–5 mm, and are therefore readily entrained in and transported by cooling air flows. These whiskers can grow on surfaces found in computer room environments, e.g. electroplated zinc surfaces, such as present on the undersides of raised floor tiles, inside air conditioning ducts and on the equipment chassis.

The prior art provides two main approaches for the detection of airborne contaminants. According to one prior art method, particulates may be collected on an air filter for subsequent counting, sizing, and identification by compositional analysis. Needless to say, this task is very arduous, cumbersome, and prone to substantial error. Also, since the cumulative number of particulates over some time period is collected and recorded, filters have the disadvantages that time-to-time variations are averaged out and information is not available in real-time.

The other commonly used technique is particle counting. In this technique, particles in a sampled airflow pass between a laser light source and a photodiode which receives the light produced by the laser. Particles in the sampled airflow scatter the laser light. The photodiode detects the interruptions in the light signal and produces electrical pulses. The height of the pulses is directly proportional to the particle size. The pulses are measured and counted by electronic circuitry. The technique allows the number and size distribution of the particulates to be recorded in real-time and enables short term variations in the number of particulates to be captured. However, these types of particle counters detect all the particles over some size range and they are unable to discriminate between different types of particles. Hence, in a dusty environment, a large number of particles will be recorded, but there may be few, or no, electrically conductive particulates, which are of particular concern to gauging the air quality as a source of short circuit failure.

SUMMARY OF INVENTION

The invention provides a method and apparatus for the real-time detection of electrically conductive contaminants in an air stream, and for effectively discriminating against nonconductive contaminants, such as dust particulates, in the same air stream.

According to one aspect of the invention, there is provided a detector for detecting conductive contaminants entrained in an airflow which comprises first and second electrically conductive meshes mounted in a spaced apart relationship to provide an operational gap therebetween. Each said mesh is sized to provide a relatively large surface for substantially intersecting the airflow, and each mesh is sufficiently porous so as to not substantially attenuate the airflow. The meshes form a part of an energized electric circuit such that the operational gap constitutes a discontinuity of the circuit. Means, including a capacitor included in the circuit containing the operational gap, are provided for releasing charge stored in the capacitor through the circuit discontinuity when a piece of conductive contaminant simultaneously contacts both meshes. Means are also provided for indicating when the capacitor has discharged, which thereby indicates the presence of an airborne conductive contaminant entrained in the airflow.

According to another aspect of the invention, there is provided a method for estimating the flux of airborne conductive contaminants entrained in an airflow. The method comprises the steps of:

providing a pair of electrically conductive meshes mounted in a spaced apart relationship to provide an operational gap therebetween, wherein each mesh is sized to provide a relatively large surface for substantially intersecting said airflow, and each mesh is sufficiently porous so as to not substantially attenuate said airflow;

establishing a voltage across said operational gap of the meshes through the use of an energized electric circuit;

discharging a capacitor through the circuit containing the operational gap when a piece of said conductive contaminant simultaneously contacts both meshes;

recording the discharge rate of the capacitor; and correlating the discharge rate with a pre-determined calibration factor to estimate the flux of airborne conductive contaminants entrained in the airflow.

The calibration factor is preferably determined by (1) capturing, at a location downstream of the electrically conductive meshes, substantially all particulates entrained in the airflow for a given period of time; (2) counting the number of conductive particulates captured in the given time period; (3) recording the number of discharges of the capacitor in the given time period; and (4) calculating the calibration factor by dividing the number of discharges by the number of counted conductive particulates.

BRIEF DESCRIPTION OF THE DRAWINGS

These and other features of the invention will become apparent from the following detailed description and the accompanying drawings, wherein.

DETAILED DESCRIPTION OF PREFERRED EMBODIMENTS

Figure 1:
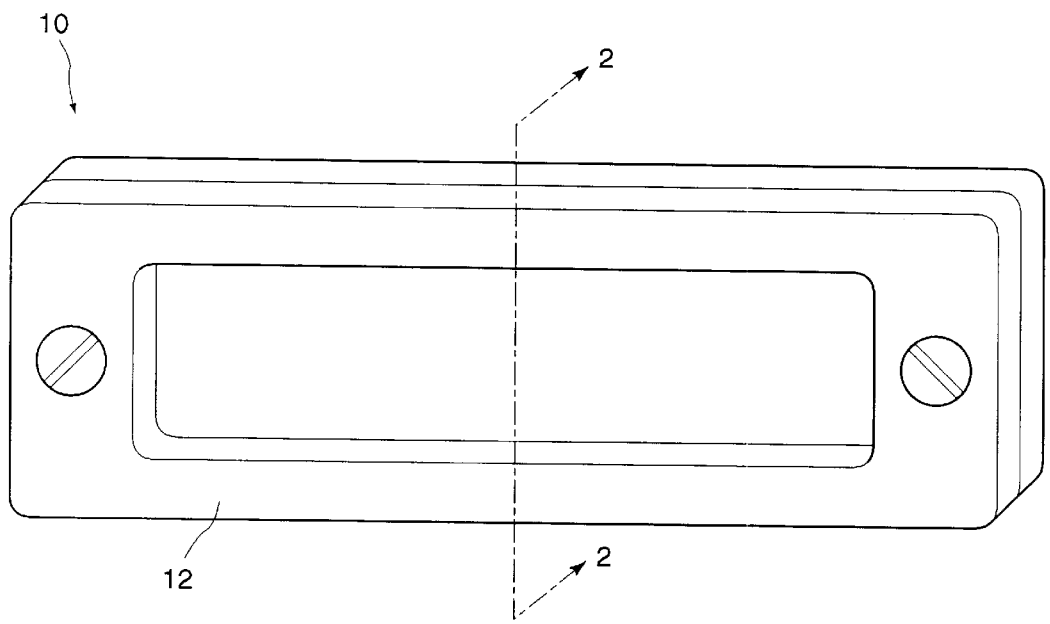
FIG. 1 is a perspective view, taken from the front, of the mechanical characteristics of a real-time airborne conductive contaminant detector in accordance with a preferred embodiment of the invention.
Figure 2:
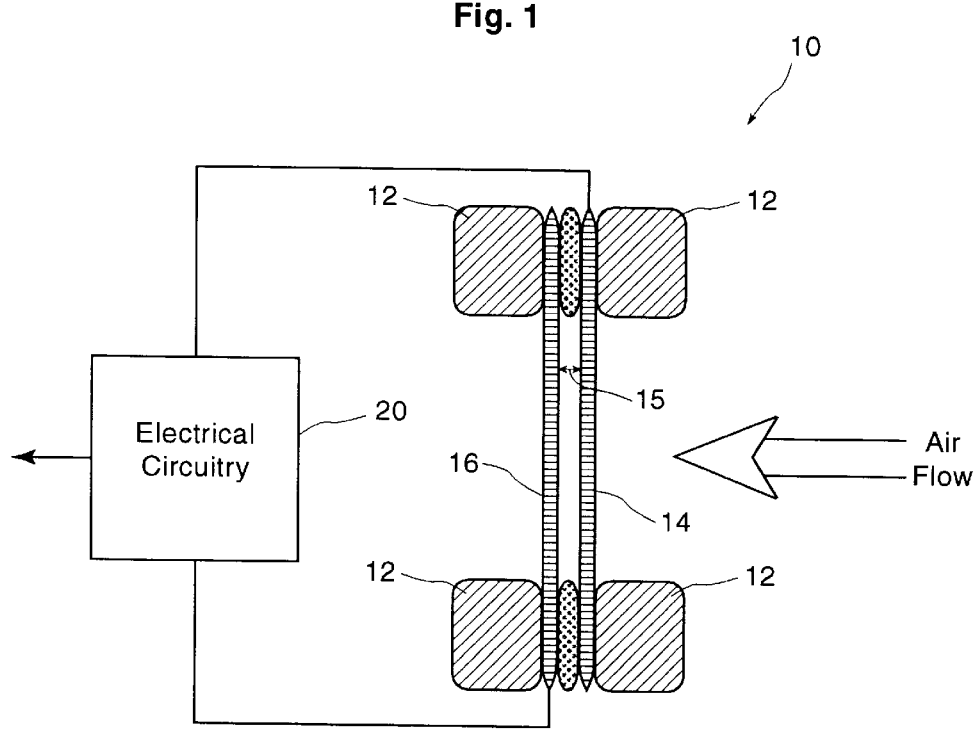
FIG. 2 is a partly cross-sectional view, partly schematic diagram of the detector shown in FIG. 1, the cross-sectional view being taken along line II—II in FIG. 1.

FIGS. 1 and 2 illustrate the mechanical characteristics of a real-time airborne conductive contaminant detector 10 (hereinafter "detector") in accordance with the preferred embodiment. The detector comprises a frame 12 used to mount two planar metallic meshes 14 and 16. The meshes 14 and 16 are maintained in a substantially parallel spaced apart relationship by a plurality of spacers 18 which are formed from a nonconductive material, such as plastic or rubber. The frame 12 is also preferably composed of a nonconductive material so that the meshes 14 and 16 are electrically isolated from each other.

The detector 10 is preferably placed within, and the meshes orientated transverse to, the cooling airstream flow of the particular electrical or computer equipment desired to be tested. For example, the detector 10, suitably sized, could be disposed within a cooling inlet of a power supply. In order not to trap particulates or attenuate the cooling airflow, the wire mesh is relatively porous, having, for example, a wire diameter of 0.25 mm and mesh aperture size of about 1.25 mm effective diameter. Alternatively, an external airflow may be induced, such by the use of a fan, in the room where the electrical equipment is located to simulate the airflow through the short circuit prone electrical equipment. Less porous meshes may thus be used, if desired.

The spacers 18 are sized to provide an operational air gap 15 between the meshes 14 and 16. The operational air gap 15 can be in the range of about 0.5 to 5 mm, and preferably about 0.75 to 1.5 mm. As described in greater detail below a d.c. voltage is established between mesh 14 and mesh 16. When a conductive piece of particulate matter, such as a metallic whisker entrained in the cooling airflow, passes between the meshes 14 and 16 and makes simultaneous contact with both meshes, a conduction path or transient short circuit is established between the meshes 14 and 16. This event is detected by electrical circuitry 20, described below, which registers the event. The detector 10 is thus selective in that only conductive contaminants, as opposed to non-conductive matter such as dust or lint, can cause a transient short circuit event which will be registered by the electrical circuitry 20.

Figure 3:
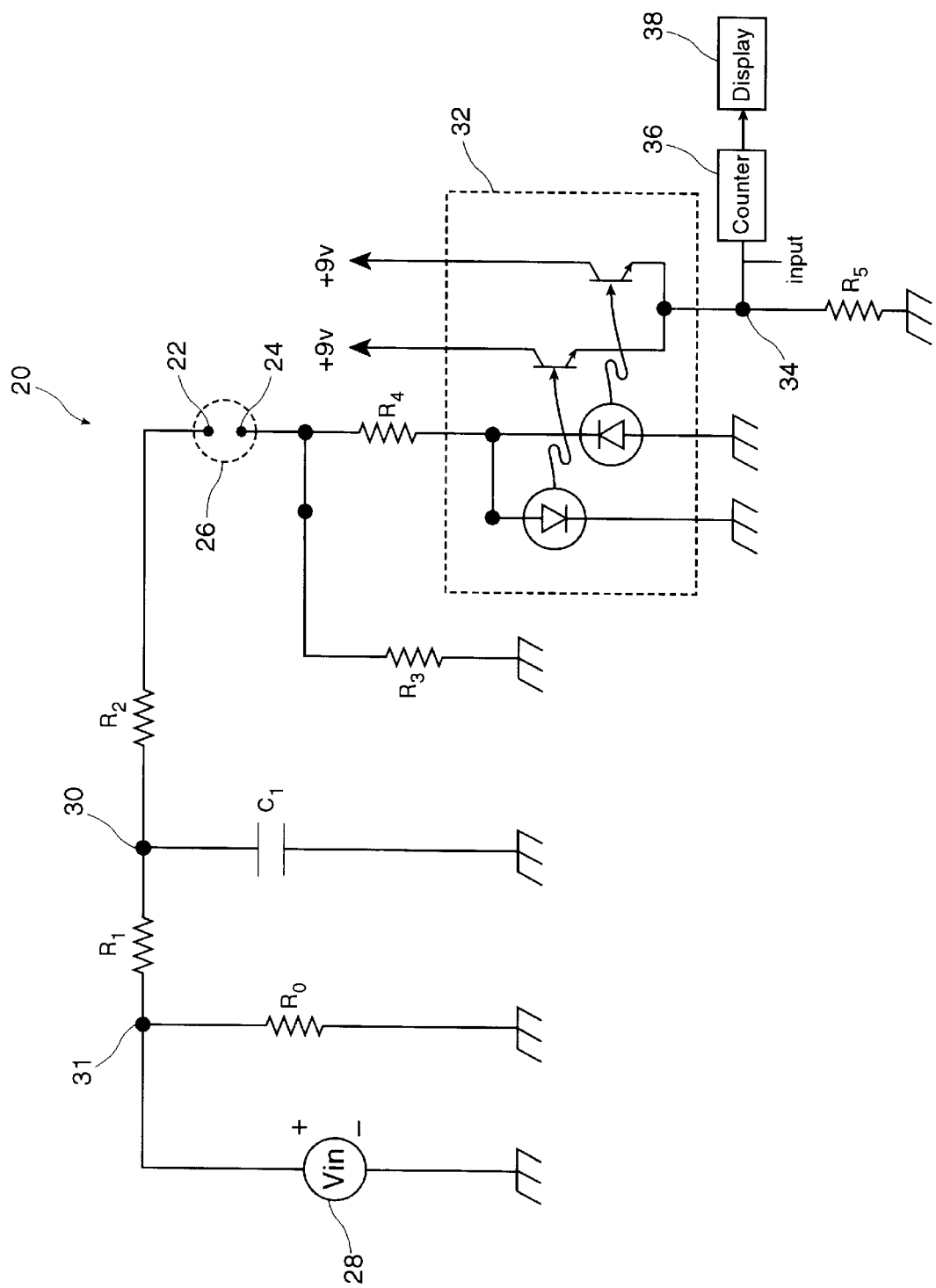
FIG. 3 is an electrical schematic diagram of the electrical characteristics and electrical circuitry employed in the detector shown in FIG. 1.

FIG. 3 shows the electrical characteristics of the detector 10 and the electrical circuitry 20 in greater detail. Mesh 14 is represented electrically by node 22 and mesh 16 is represented by node 24. Gap 26 between nodes 24 and 26 represents the air gap 15 between the meshes.

The circuitry 20 comprises a high voltage source $V_{IN}$ (28). For example, a 1 kV, 100 mA variable power supply could be used to provide voltage source 28. A first resistor $R_1$, is connected between a positive output of the power supply 28 and a central node 30. A second resistor $R_2$ is connected between the central node 30 and node 22 which represents the mesh 14. $R_2$ is a power or high current capacity resistor which preferably is one or two orders of magnitude smaller than $R_1$ in ohmic value. A capacitor $C_1$ is also connected between the cental node 30 and ground. A resistor $R_0$ may be connected to ground as at node 31. In the event that voltage source 28 is disconnected from circuit, the capacitor $C_1$ will discharge to ground through the series combination of resistors $R_1$ and $R_0$.

Node 24, representing mesh 16, is connected to a second power resistor $R_3$, which provides a conduction path to ground. $R_3$ is also preferably one or two orders of magnitude smaller than $R_1$ and approximately 20% less in ohmic value than $R_2$. An optical isolation circuit 32, as is well known in the art, is disposed in parallel with resistor $R_3$ and connected to node 24 through resistors $R_4$ as shown. The optical isolation circuit is used to sense the current flowing through $R_3$ yet isolate the low voltage output of circuitry 20 from the high power operation of the circuit, as explained more fully below.

The operation of the circuit 20 is now described. In a steady state operation of the circuit, the air gap 26 between the nodes 22 and 24, corresponding to the air gap 15 between meshes 14 and 16, presents an open circuit condition such that no current flows through $R_3$. Accordingly, node 30 exhibits a voltage equal to $V_{IN}$, e.g. 500 volts, and capacitor $C_1$ is in a fully charged state.

Figure 4:
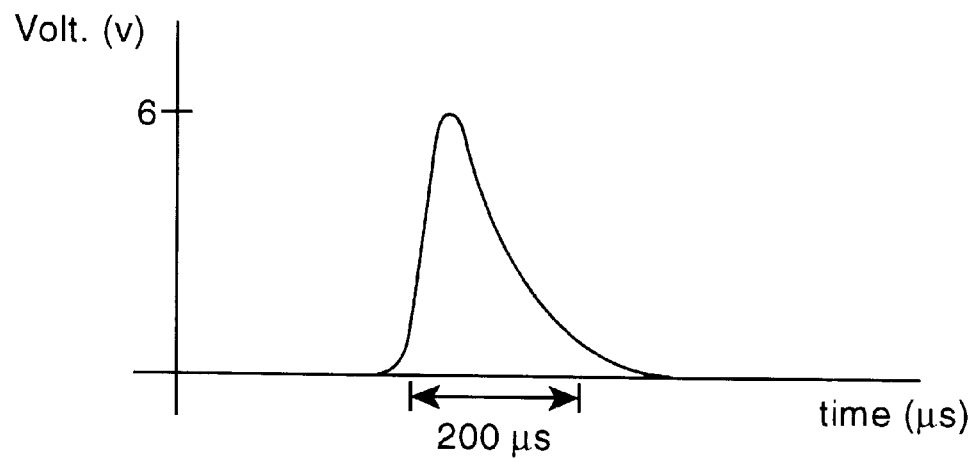
FIG. 4 is a diagram of an output voltage waveform produced by the electrical circuitry shown in FIG. 3.

When a piece of conductive particulate matter, such as a metallic whisker, simultaneously contacts both meshes 14 and 16, a conduction path or transient short circuit is established between nodes 22 and 24. The capacitor $C_1$ will thus discharge through $R_2$ and $R_3$ to ground since the resistance through this path is very low. Resistor $R_3$ provides a voltage which is a sample of the current flowing between nodes 22 and 24 representing meshes 14 and 16. This voltage is sensed by the optical isolation circuit 32 through resistor $R_4$. The optical isolation circuit provides a low voltage signal at an output node 34 reflecting the capacitor discharge or current spike. FIG. 4 shows an example of the output waveform at node 34 for one specific transient short circuit event in circuit 20 (in circumstances where $V_{IN}$=500 V, $C_1$=2 uF, and the resistor values correspond to that shown in Table 3.1, below, for the "medium" speed of operation).

Once the transient short circuit event has elapsed, and capacitor $C_1$ has discharged its energy, and the arc current between nodes 22 and 24 has extinguished, the normal or steady state open circuit condition between nodes 22 and 24, corresponding to meshes 14 and 16, is re-established and capacitor $C_1$ is re-charged by voltage source 28 through resistor $R_1$. It will be noted that the charge and discharge rates of capacitor $C_1$ are substantially determined by resistors $R_1$ (charge) and $R_2$ and $R_3$ (discharge) for a given capacitance. Varying the values of these resistances, such as shown in Table 3.1 below, will affect the charging and discharging rate of capacitor $C_1$, and thus the duration or width of the pulse produced at output node 34 and the "operating speed" of circuit 20. For ambient air environments which contain a relatively high concentration of conductive particulate contamination, it may thus be desirable to select component values to provide a "fast" operating speed.

TABLE 3.1

| | SPEED OF OPERATION | | |
| --- | --- | --- | --- |
| Element | Slow | Medium | Fast |
| $R_1$ | 100 kΩ | 30 kΩ | 10 kΩ |
| $R_2$ | 500 Ω | 50 Ω | 10 Ω |
| $R_3$ | 100 Ω | 10 Ω | 2 Ω |
| $R_4$ | 22 kΩ | 22 kΩ | 22 kΩ |
| $R_5$ | 1 kΩ | 1 kΩ | 1 kΩ |
| $C_1$ | 2–10 µF | 2–10 µF | 2–10 µF |

The voltage pulse produced at output node 30, such as shown in FIG. 4, can be amplified, if necessary, and fed into a trigger circuit or counter 36 (FIG. 3) such as an edge-triggered counter or edge-triggered shift register in order to count the number of pulses in a given unit of time. The pulse count could then be displayed on a display 38 to show the transient short circuit event rate in substantially real-time.

Alternatively, the contents of counter 36 could be transferred to a memory or computer (not shown) to prepare and/or display a histogram of transient short circuit event rates using the collected data.

The optical isolation circuit 32 isolates the power and signal grounds in the system, thus reducing the possibility of noise pulses causing false counts.

Figure 5:
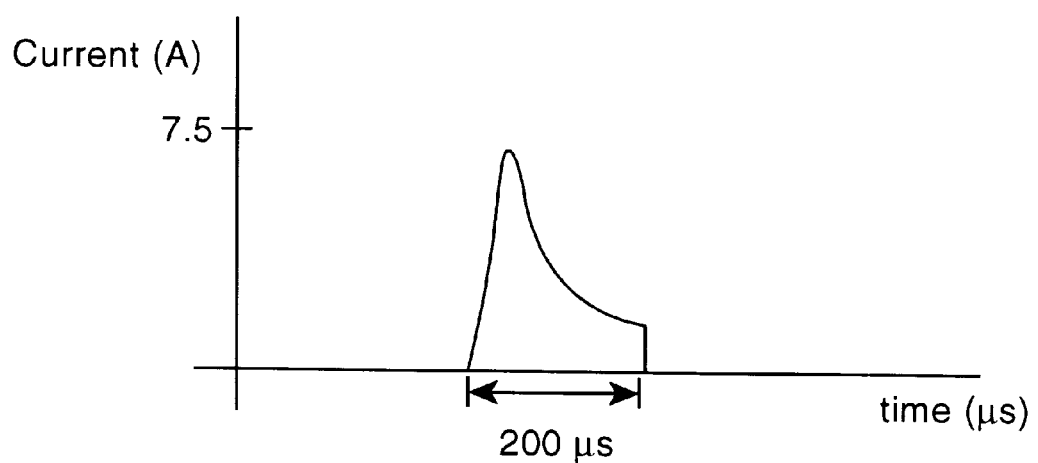
FIG. 5 is a diagram of a current discharge waveform produced by the electrical circuitry shown in FIG. 3.

The circuit 20 has been described operating in a "high energy mode", where $V_{IN}$ supplies over 500 volts. In the high energy mode, a conductive piece of particulate matter, such as a metal whisker, which simultaneously contacts meshes 14 and 16 is vaporized, and ionizes the air surrounding the particulate in the air gap 15 between the meshes. This enables an electrical arc to be maintained between the meshes, which is readily visible upon the occurrence of a transient short circuit event. This phenomenon can also be noticed by examining a current wave form, shown in FIG. 5, of central node 30 during a transient short circuit event. As seen in FIG. 5, the current pulse has a duration of approximately 200 microseconds, whereas the time in which the metal whisker is estimated to actually simultaneously contact both meshes 14 and 16 is much shorter, e.g. 1–10 microseconds, depending on the airflow speed, the length of the particulate, and the gap spacing.

Accordingly, for the high energy mode of operation, the capacitor must have sufficient stored energy to cause ionization of the air between the two screen meshes and hence the generation of the arc therebetween. This is estimated to require an energy level in the order of about 0.5 to 5.0 joules. Hence, the value of $V_{IN}$, capacitance $C_1$, and resistors $R_2$ and $R_3$ should be selected to ensure a peak discharge current sufficient to vaporize the metal whisker and ionize the surrounding air. By way of example, the peak current of the discharge current pulse shown in FIG. 5 is approximately 7.5 amperes when the circuit 20 was configured as mentioned above (i.e., $V_{IN}$=500 V, $C_1$=2 uF, and the resistor values correspond to that shown in Table 3.1 for the "medium" speed of operation). It is anticipated, however, that a much smaller peak discharge current, e.g. 50–60 mA, may be sufficient to fuse or melt a typical metal whisker. The minimum peak discharge current required to do so will of course vary depending on the size, weight and composition of the metallic particulate.

Resistor $R_1$ also plays a role in limiting the arc current to a value which ensures that the electrical arc between nodes 22 and 24 will extinguish after capacitor $C_1$, has discharged all of its energy. This current is estimated to be about 50 mA or so. Likewise, resistor $R_2$ limits the arc current to a controlled peak value sufficient to sustain the arc, as described above.

The circuit 20 can also operate in a "low energy mode", with $V_{IN}$ providing less than about 50 volts. In the low energy mode, the circuit 20 produces a much lower discharge current, e.g., less than 50 mA. The metallic whiskers which come into simultaneous contact with both meshes generally do not ionize the surrounding air to create a discharge arc across the air gap 15 between meshes 14 and 16. Thus, the duration of the transient short circuit event will only last for as long as it takes capacitor $C_1$ to substantially discharge. Accordingly, in the low energy mode, the output at node 34 is a discharge pulse of much shorter duration then the duration of the pulse in the high energy mode of operation of circuit 20.

Due to the substantial porosity of the meshes 14 and 16, only a small portion of the electrically conductive particles flowing through the detector 10 contact the meshes and are registered by the electrical circuitry 20 as described above. Therefore, the detector 10 should be calibrated for use. One way of calibrating the detector is to initially deploy an air filter behind the detector 10 to trap all particles, conductive or not, passing through the detector for a given period of time. By recording the number of transient short circuit events over the given period of time and, using a microscope, counting the number of metallic particles trapped by the filter, the detection efficiency of the detector 10 can be estimated within the tolerance of the error in counting the collected metallic particulates. Using such a method, the applicants estimate the detection efficiency of the detector 10 to be about 0.1%, i.e. 1 count for every 1,000 electrically conductive particulates passing through, when the detector 10 was configured to have a mesh air gap of about 0.8 mm, $V_{IN}$=500 V, using zinc whiskers having an unknown length distribution and an average length of about 1 mm. In this manner, the flux of electrically conductive particles in a cooling airstream can be estimated.

It will be seen from the foregoing that the detector 10 provides a number of advantages. First, it will be noted that only conductive particulates entrained in a cooling air stream are detected. Thus, a more accurate indication of the quality of the air as a source of electrical equipment short circuit failure, is obtained.

Second, the conductive particulates are detected in real time. A counter may be employed to count the number of transient short circuit event, or alternatively, in the high energy mode of operation of circuit 20, the transient short circuit events may be visibly detected due to the visible electrical arc flashes which are generated between meshes 14 and 16.

Third, the detector 10 can conveniently be used in-line, i.e., in the path of the cooling air stream of the electrical equipment under test, and is independent of orientation. Detection of the conductive particulates is substantially non-destructive for most particles and the sampling is isokinetic at all flow speeds since the air flow is not significantly perturbed or attenuated. Hence, the detector 10 may be used concurrently, upstream or downstream, with electrical equipment being measured for short circuit susceptibility.

Fourth, the air gap or spacing 15 between the meshes 14 and 16 can be adjusted to detect conductive particulates of a specific minimum length that are of particular concern for certain types of electrical equipment. In addition, the dimensions of the detector 10 can be readily adapted to cover the air intake (or outlet) of the electrical equipment under test by using frames and meshes of suitable size. This enables the total number of conductive particulates flowing through a relatively large opening to be monitored in real time.

The preferred embodiment of the invention has been described herein with a certain degree of particularity for the purposes of description and illustration. However, it will be appreciated that a number of variations can be made to the preferred embodiment without departing from the spirit of the invention.

What is claimed is:

1. A detector for detecting conductive contaminants entrained in an airflow, said detector comprising:

first and second electrically conductive meshes mounted in a spaced apart relationship to provide an operational gap therebetween, wherein each said mesh is sized to provide a relatively large surface for substantially intersecting said airflow and each said mesh is sufficiently porous so as to not substantially attenuate said airflow;

an energizable electric circuit, said meshes forming a part of said circuit such that said operational gap constitutes a discontinuity thereof;

means, including a capacitor as part of said circuit containing said operational gap, for releasing a charge stored in said capacitor through said circuit discontinuity when one of said conductive contaminants simultaneously contacts said first and second meshes; and means for indicating a discharge of said capacitor and thereby the presence of one of said airborne conductive contaminants entrained in said airflow.

2. The detector according to claim 1, wherein said capacitor is sufficiently energized by said electric circuit to discharge sufficient current to fuse, melt or vaporize said one of said conductive contaminant which simultaneously contacts said first and second meshes to thereby generate an electric arc between said first and second meshes.

3. The detector according to claim 2 further comprising means for extinguishing said electric arc.

4. The detector according to claim 1 wherein said indicating means comprises a means for recording or registering the number of discharges of said capacitor in a given period of time.

5. The detector according to claim 1 including means for automatically recharging said capacitor after it has discharged its stored charge.

6. The detector according to claim 5 wherein said automatic recharging means comprises a resistor connected to a node of said electric circuit common to said capacitor and to said portion of said circuit containing said operational gap.

7. The detector according to claim 1 including an optical isolation circuit connected in series with said meshes for generating an isolated low voltage output indicative of the discharge of said capacitor.

8. A method for estimating the flux of airborne conductive contaminants entrained in an airflow, said method comprising the steps of:

providing a pair of electrically conductive meshes mounted in a spaced apart relationship to provide an operational gap therebetween, wherein each said mesh is sized to provide a relatively large surface for substantially intersecting said airflow, and each said mesh is sufficiently porous so as to not substantially attenuate said airflow;

establishing a voltage across said operational gap of said meshes through the use of an energized electric circuit;

discharging a capacitor through said circuit containing said operational gap substantially each time one of said conductive contaminants simultaneously contacts said meshes;

recording each such discharge of said capacitor; and correlating the number of recorded discharges of said capacitor with a pre-determined calibration factor to thereby estimate the flux of airborne conductive contaminants entrained in said airflow.

9. The method according to claim 8 wherein said calibration factor is determined by:

capturing, at location downstream of said electrically conductive meshes, substantially all particulates entrained in said airflow for a given period of time;

counting the number of conductive particulates captured in said given period of time;

recording the number of discharges of said capacitor in said given period of time; and calculating said calibration factor by dividing the number of recorded discharges by the number of counted conductive particulates.

10. A detector for detecting conductive contaminants entrained in an airflow, said detector comprising:

first and second electrically conductive meshes mounted in a spaced apart relationship to provide an air gap therebetween, wherein each said mesh is sized to provide a relatively large surface for substantially intersecting said airflow, each said mesh is sufficiently porous so as to not substantially attenuate said airflow, and said air gap between said meshes is dimensioned to enable conductive contaminants of a pre-determined length to simultaneously contact both meshes;

electrical circuitry for establishing a voltage between said first and second meshes such that said air gap represents a circuit discontinuity, said circuitry including a capacitor as part of said circuitry containing said circuit discontinuity and means for discharging said capacitor of a stored charge through said circuit discontinuity when one of said conductive contaminants simultaneously contacts said first and second meshes; and means for indicating a discharge of said capacitor and thereby the presence of one of said airborne conductive contaminants entrained in said airflow.

11. The detector according to claim 10 including means for automatically recharging said capacitor after it has discharged its stored charge.

12. The detector according to claim 11 wherein said automatic recharging means comprises a resistor connected to a node of said electric circuit common to said capacitor and to said portion of said circuit containing said operational gap.

13. The detector according to claim 10, wherein said capacitor is sufficiently energized to discharge sufficient current to vaporize said one of said conductive contaminant which simultaneously contacts said first and second meshes to thereby generate an electric arc between said first and second meshes.

14. The detector according to claim 13 further comprising means for extinguishing said electric arc.

15. The detector according to claim 10 wherein said indicating means comprises a means for recording or registering the number of discharges of said capacitor in a given period of time.

16. The detector according to claim 10 including an optical isolation circuit connected in series with said meshes for generating an isolated low voltage output cindicative of the discharge of said capacitor.

17. The detector according to claim 1, wherein said conductive contaminants are metallic whiskers having a length of approximately 0.5 to 5 mm and said meshes are spaced apart by a distance in the range of 0.5 to 5 mm.

18. The method according to claim 8, wherein, said conductive contaminants are metallic whiskers having a length of approximately 0.5 to 5 mm and said meshes are spaced apart by a distance in the range of 0.5 to 5 mm.

19. The detector according to claim 10, wherein said predetermined length is in the range of approximately 0.5 to 5 mm.

* * * * *